United States Patent
Friese et al.

(10) Patent No.: US 6,299,805 B1
(45) Date of Patent: Oct. 9, 2001

(54) BORON NITRIDE SEALING ELEMENT

(75) Inventors: Karl-Hermann Friese, Leonberg; Helmut Weyl, Schwieberdingen; Anton Hans, Stuttgart, all of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/341,449

(22) PCT Filed: Oct. 22, 1998

(86) PCT No.: PCT/DE98/03099

§ 371 Date: Jul. 9, 1999

§ 102(e) Date: Jul. 9, 1999

(87) PCT Pub. No.: WO99/24377

PCT Pub. Date: May 20, 1999

(30) Foreign Application Priority Data

Nov. 12, 1997 (DE) .............................. 197 50 107

(51) Int. Cl.$^7$ .............................. C04B 35/583; F16J 15/34
(52) U.S. Cl. .............. 264/37.29; 264/109; 264/233; 277/627; 277/650; 277/935; 277/936; 277/939; 277/940; 423/290
(58) Field of Search ................................ 264/37, 29, 109, 264/233; 423/290; 277/627, 650, 935, 936, 939, 940

(56) References Cited

U.S. PATENT DOCUMENTS 4,205,858 * 6/1980 Shimazaki et al. .............. 277/936 X
5,571,379    11/1996 Derrick .

FOREIGN PATENT DOCUMENTS 21 22 621    11/1972 (DE) .
 1321033 *  6/1973 (DE) .
63-46287 *  2/1988 (JP) .

OTHER PUBLICATIONS

Database WPI Week 8626, Derwent Publications, Ltd., London, GB; AN 86–167200 XP002095656, "Sealing Resin Composition with High Coefficient of Thermal Conductivity".

* cited by examiner

Primary Examiner—Leo B. Tentoni
(74) Attorney, Agent, or Firm—Kenyon & Kenyon

(57) ABSTRACT

A sealing member is produced from form-pressed boron nitride powder, while adding an inorganic or organic binding agent. Such boron nitride powder is obtained during the machining of boron nitride blocks composed of hexagonal boron nitride. This powder can be fractionated according to particle size and the particle size desired for manufacturing the sealing member can be separated out.

16 Claims, 2 Drawing Sheets

BORON NITRIDE SEALING ELEMENT

BACKGROUND OF THE INVENTION

The present invention relates to boron nitride sealing members which are particularly suitable for sealing off an oxygen reference chamber with respect to a lambda-probe space containing exhaust gas, as well as a method for its manufacture.

Boron nitride (BN) gaskets, formed by machining from hot-pressed BN blocks made of hexagonal boron nitride material, fulfill the necessary resistance to gasoline, but are too expensive as a mass production product because of the costly manufacture.

Figure 1:
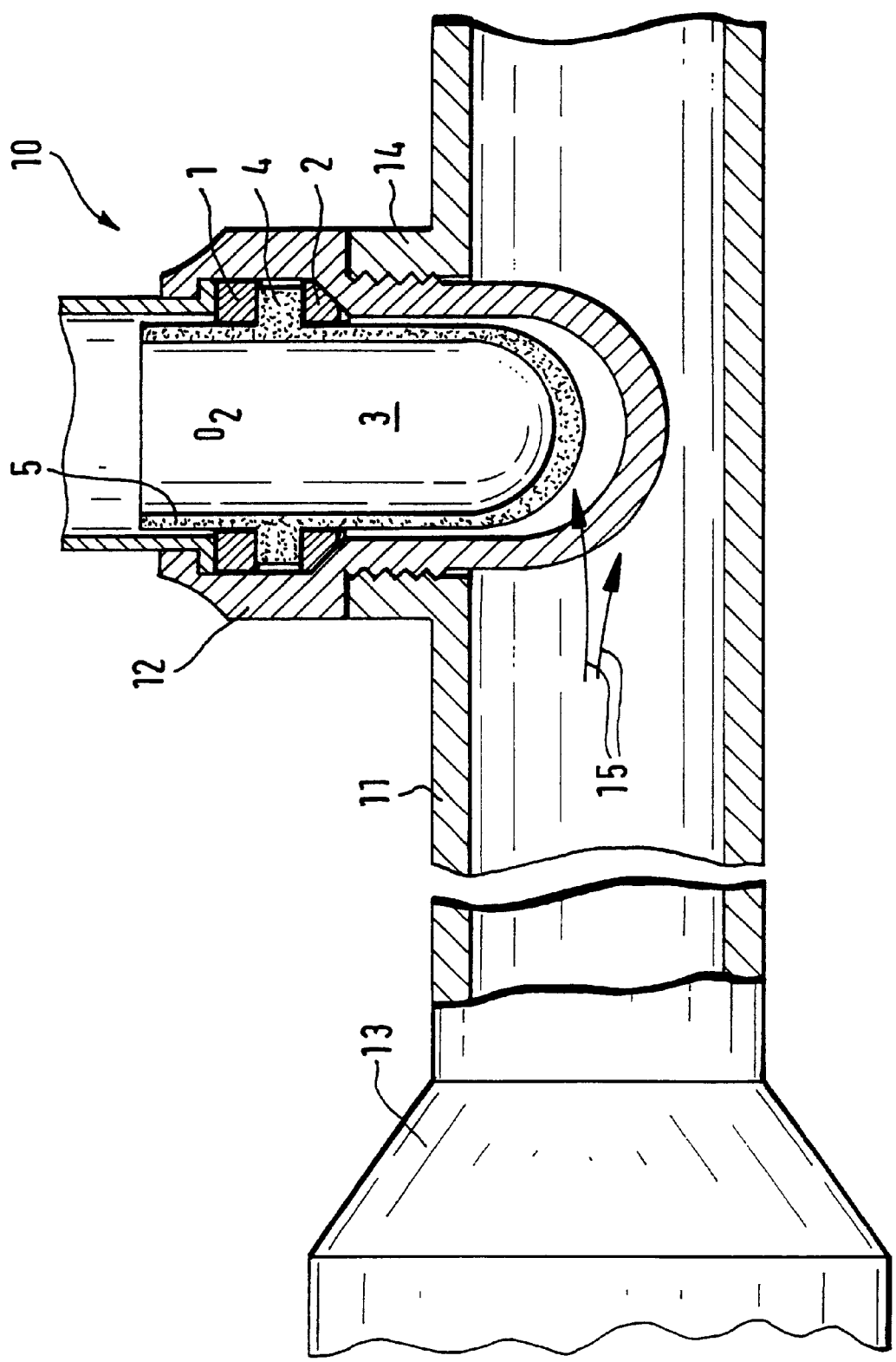

The attached FIG. 1 shows schematically a lambda probe, known illustratively from the U.S. Pat. No. 5,571,379, which is situated in an exhaust-gas path of an internal combustion engine. The probe, designated generally by 10, is located within a housing 12 that is screwed into a flange 14 of an exhaust pipe 11 leading from the engine 13. Situated within a cylindrical zirconium-dioxide probe substrate 5 is an oxygen ($O_2$) reference chamber 3 which projects into a porous part of housing 12 seated in exhaust pipe 11. So that the measuring results are not invalidated, a peripheral flange 4 of substrate 5 is sealed off with respect to housing 12 by gaskets 1,2 made of boron nitride, so that no exhaust gas 15 can reach oxygen reference chamber 3. As already mentioned, in the U.S. Patent indicated above, the BN gaskets are machined from hot-pressed boron nitride blocks, and thus have the disadvantage of the high production costs already described. It should be mentioned that the design of the oxygen sensor or of lambda probe 10, selected in FIG. 1 for the related art, can be implemented just the same with boron-nitride sealing members formed according to the invention, i.e., that the construction shown in FIG. 1 can also be used in conjunction with the invention.

SUMMARY OF THE INVENTION

In light of what has been said above, the object of the present invention is to make possible boron nitride sealing members which are less expensive to produce and are particularly suitable for sealing off an oxygen reference chamber with respect to a space of a lambda probe containing exhaust gas, as well as a cost-effective method for manufacturing them.

According to one essential aspect of the invention, this objective is achieved in that the sealing member has form-pressed boron nitride powder, obtained by comminution from hot-pressed hexagonal boron nitride material, and an added binding agent. Such boron nitride powder, falling off during the production of boron nitride members that are machined from hot-pressed boron nitride blocks made of hexagonal boron nitride material, can be fractionated according to particle categories. The particles have good flowability, and are made of hot-pressed hexagonal boron nitride which has a relatively high density (about 2.2 g/cm$^3$). According to the invention, this powder is pressed, while adding a binding agent, to form a sealing member.

DETAILED DESCRIPTION OF THE INVENTION

The selected particle size of the boron nitride powder is preferably in the range of approximately 5 to 30 μm particle diameter. A suitable organic binding agent is wax which can be easily evaporated, and the amount of binding agent is a function of the selected particle size of the boron nitride powder. For example, organic binding agent in an amount of 0.1% by weight is mixed with the boron nitride powder.

An inorganic binding agent, like the familiar fire-resistant binding agents such as aluminum phosphate which is likewise admixed to the boron nitride powder in a very small quantity, can also be used as an additive for consolidating the pressed object.

The use of boron nitride powder from which free boron oxide has been washed out, e.g., the type HSS of ESK Elektroschmelzwerk Kempten, is advantageous.

According to another essential aspect of the present invention, the objective stated above is fulfilled by a method for manufacturing boron nitride sealing members, in particular for sealing off an oxygen reference chamber with respect to a lambda-probe space containing exhaust gas, which is characterized by the following steps:

make available a powdery waste material which falls off during the production of boron nitride components made by machining from hot-pressed boron nitride blocks composed of hexagonal boron nitride material;

fractionate the powdery waste material according to particle size;

separate a particle-size range desired for producing the boron nitride sealing member;

mix the powder of the separated particle-size range with a small amount of an organic or inorganic binding agent;

form-press the mixture to form a sealing member having a desired shape; and dry, while evaporating the volatile matter contained in the binding agent.

The method of the present invention can be used particularly advantageously for the cost-effective production of boron nitride sealing devices in planar oxygen sensors, especially in a sandwich type of construction as an intermediate layer between two steatite packets.

Figure 2:
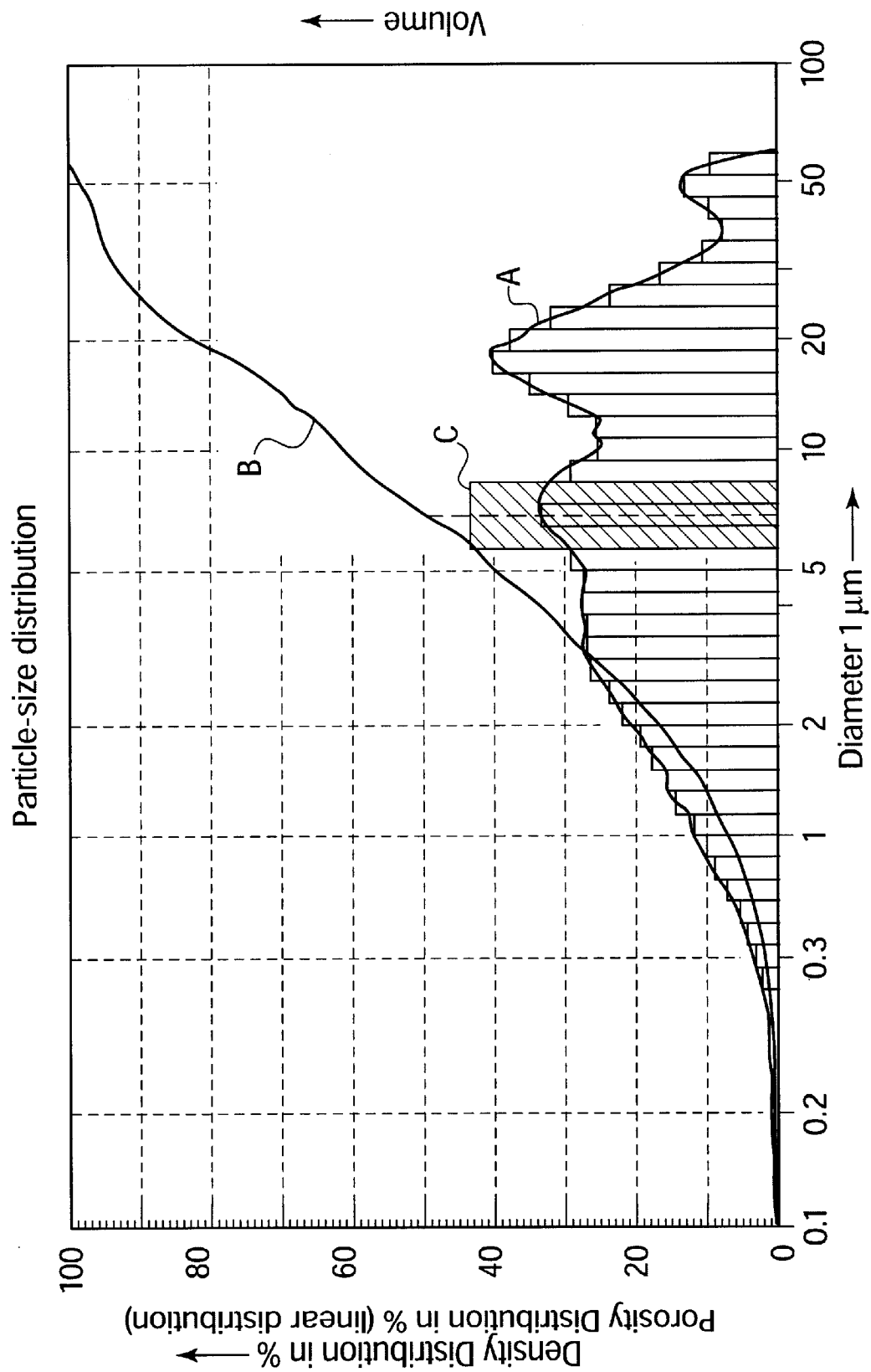

FIG. 1, in a schematic cross-section, shows the known lambda probe, already described, for which the invention can be used, FIG. 2 shows graphically a distribution of the particle sizes of powdery waste material which is formed during the machining of hot-pressed boron nitride blocks made of hexagonal boron nitride.

In FIG. 2, curve A shows an average density distribution in percentage for particle diameters in μm of a specific boron nitride powder, and curve B indicates the volume of the powder. The boron nitride powder type HSS of ESK Elektroschmelzwerk Kempten mentioned above, from which free $B_2O_3$ was washed out, was selected as an example. FIG. 2 shows that the particle-size distribution has clearly pronounced maxima, e.g., at a particle diameter of approximately 7.5 μm, at a particle diameter of approximately 18 μm, and a particle diameter of approximately 50 μm. To produce sealing members form-pressed from such a boron nitride powder, particles which, for example, fall into a particle-size range C, indicated by hatching, are separated and are pressed together with a small amount of an organic or inorganic binding agent to form the desired shape. After that, the volatile matter contained in the binding agent is evaporated and the boron nitride sealing member thus produced is packed in a sandwich type of construction between two steatite packets. In this form, the boron nitride sealing member can then be used for sealing off a lambda probe, e.g., such a probe as is shown in FIG. 1. However, the boron nitride sealing members produced according to the method of the present invention are preferably used for sealing off planar oxygen sensors.

What is claimed is:

1. A boron nitride sealing member for sealing off an oxygen reference chamber with respect to a lambda-probe space containing exhaust gas, the sealing member comprising:
- a form-pressed hexagonal boron nitride powder, the boron nitride powder containing boron nitride particles from a selected particle-size fraction, and from which free boron oxide has been washed out, the boron nitride powder being obtained by comminution from hot-pressed boron nitride material; and
- an added binding agent.

2. The boron nitride sealing member according to claim 1, wherein the boron nitride powder has a particle size in the range of about 5 to 30 μm particle diameter.

3. The boron nitride sealing member according to claim 1, wherein the binding agent contains an organic binder.

4. The boron nitride sealing member according to claim 3, wherein the binding agent contains a volatile wax which is easily evaporated.

5. The boron nitride sealing member according to claim 1, wherein the amount of binding agent is selected as a function of the particle size of the boron nitride powder, the particle size being in the range of about 5 to 30 μm particle diameter.

6. The boron nitride sealing member according to claim 1, wherein approximately 0.1% by weight of organic binding agent is admixed to the boron nitride power.

7. The boron nitride sealing member according to claim 1, wherein the binding agent contains an inorganic fire-resistant binder.

8. The boron nitride sealing member according to claim 7, wherein the inorganic fire-resistant binder contains aluminum phosphate.

9. The boron nitride sealing member according to claim 7, wherein the inorganic fire-resistant binder is contained in a very small quantity in the sealing member.

10. A method for manufacturing a boron nitride sealing member used for sealing off an oxygen reference chamber with respect to a lambda-probe space containing exhaust gas, comprising the steps of:
- making available a powdery waste material which falls off during the production of boron nitride components made by machining from hot-pressed boron nitride blocks composed of hexagonal boron nitride material;
- fractionating the powdery waste material according to particle size;
- separating a particle-size range desired for producing the boron nitride sealing member;
- mixing the powder of the separated particle-size range with a small amount of an organic or inorganic binding agent;
- form-pressing the mixture to form a sealing member having a desired shape; and
- drying, while evaporating volatile matter contained in the binding agent.

11. The manufacturing method according to claim 10, wherein the desired particle size is in the diameter range of about 5 to 30 μm.

12. The manufacturing method according to claim 10, further comprising the step of washing out free boron oxide from the boron nitride powder.

13. The manufacturing method according to claim 10, wherein organic binding agent is fed at about 0.1% by weight during the mixing.

14. The manufacturing method according to claim 13, wherein the binding agent contains volatile wax which is easily evaporated.

15. The manufacturing method according to claim 10, wherein a very small quantity of inorganic binding agent is added during the mixing.

16. The manufacturing method according to claim 15, wherein the inorganic binding agent contains aluminum phosphate.

* * * * *